United States Patent [19]

Rosenstatter

[11] Patent Number: 5,482,462
[45] Date of Patent: Jan. 9, 1996

[54] DENTAL HANDPIECE

[75] Inventor: Otto Rosenstatter, Seeham, Austria

[73] Assignee: Imtec Innovative Medizintechnik Gesellschaft m.b.H., Hallein, Austria

[21] Appl. No.: 204,334

[22] Filed: Mar. 14, 1994

[30] Foreign Application Priority Data

Sep. 13, 1991 [AT] Austria .................... 1838/91

[51] Int. Cl.⁶ .................... A61C 1/08; A61C 1/10; A61C 1/12; A61C 17/02
[52] U.S. Cl. .................... 433/126; 433/84
[58] Field of Search .................... 433/84, 85, 115, 433/126, 29

[56] References Cited

U.S. PATENT DOCUMENTS

| | | | |
|---|---|---|---|
| 4,080,737 | 3/1978 | Fleer | 433/126 |
| 4,107,846 | 8/1978 | Fleer et al. | |
| 4,182,038 | 1/1980 | Fleer | 433/126 X |
| 4,213,756 | 7/1980 | Reich et al. | |
| 4,260,382 | 4/1981 | Thomson | 433/126 |
| 4,514,172 | 4/1985 | Behringer | 433/126 |
| 4,957,483 | 9/1990 | Gonser et al. | 433/126 X |
| 5,039,304 | 8/1991 | Heil | 433/126 |
| 5,156,546 | 10/1992 | Frank et al. | 433/25 |

FOREIGN PATENT DOCUMENTS

| | | |
|---|---|---|
| 359632 | 11/1980 | Austria . |
| 370979 | 5/1983 | Austria . |
| 2448341 | 9/1980 | France . |
| 2855682 | 7/1980 | Germany . |
| 157596 | 11/1982 | Germany . |
| 8510667 | 9/1986 | Germany . |
| 3930114 | 11/1990 | Germany . |
| 580422 | 10/1976 | Switzerland . |
| 2072779 | 10/1981 | United Kingdom . |

*Primary Examiner*—Nicholas D. Lucchesi
*Attorney, Agent, or Firm*—Wenderoth, Lind & Ponack

[57] ABSTRACT

A dental handpiece includes an end grip member having a configuration and shape to be gripped by an operator, such as a dentist, during use. The end grip member has a first end to be connected to a supply and a second end having therein a recess. At least one coolant line to receive coolant when the end grip member is connected to the supply extends through the end grip member. A plurality of tool holders support respective different tools and are interchangeable selectively connectable to and detachable from the second end of the end grip member. Each tool holder has a first end to carry a respective tool and a second end having an extension extended into the recess in the second end of the end grip member when such tool holder is connected thereto. The extension is configured to block coolant passage or to allow coolant passage through a selected portion of the coolant line.

16 Claims, 5 Drawing Sheets

FIG. 1a
FIG. 1b
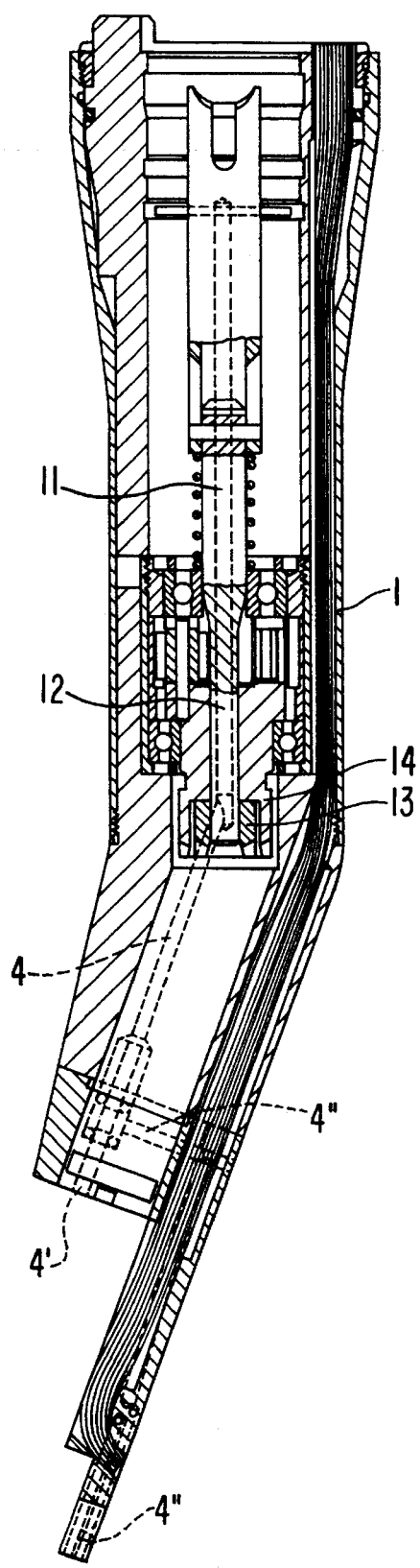
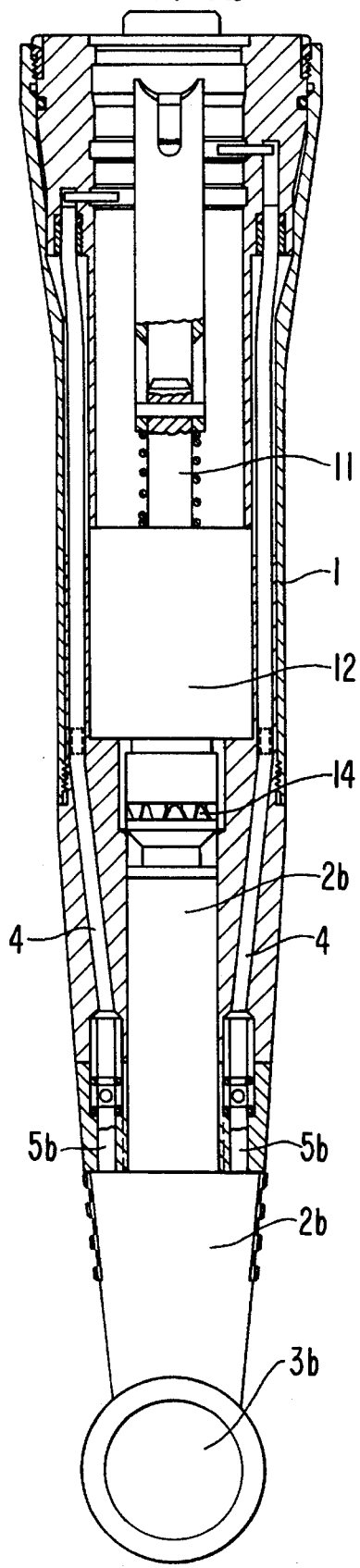

DENTAL HANDPIECE

BACKGROUND OF THE INVENTION

The invention relates to a dental handpiece comprising an end grip member to which can be connected selectively different neck members that carry head members to hold tools, whereby at least one coolant line extends through the end grip member.

It is well known to design such handpieces in a manner such that an end grip member can be connected to different neck members. In so doing, however, it is always provided that the coolant lines, which extend through the end grip member and terminate at an interface between end grip member and neck member, are continued in the neck member (cf. AT-A-359 632, AT-A- 370 979).

SUMMARY OF THE INVENTION

In contrast, the object of the invention is to provide a dental handpiece having a end grip member can be used as universally as possible. In this context it is provided according to the invention that the neck member of each of a plurality of different tool holders is provided with at least one extension that extends into a recess in the end grip member and closes a coolant line extending therethrough. With such feature according to the invention it is no longer necessary to change the end grip member of the dental handpiece when there is a transfer between neck members having different coolant requirement. The proposal according to the invention allows, above all, a coolant line extending through the end grip member to terminate not only at a fixed point, but also to provide two or more exit points for such coolant line, whereby the flow of coolant does or does not continue into the neck member, depending on the type of neck member used.

There is known from DE-U 85 10 667 a dental handpiece wherein an end grip member includes an arm which reaches under the neck member and extends over the entire length of the neck member and which has an end having outlet ports for cooling water and cooling air. The invention can also be employed with such an arrangement, in order to guide the cooling medium selectively through the neck member or the arm reaching under the neck member.

Up to this point, it has been assumed in the presentation of the invention that the extension that is provided at the neck piece closes a coolant line which is normally open in the end grip member. It is just as possible to close such line in the normal case by means of a valve which is opened by insertion of the extension of the neck member.

BRIEF DESCRIPTION OF THE DRAWINGS

Details of the invention are explained in the following with reference to the accompanying drawings, wherein:

FIGS. 1a and 1b are sectional side and top views of the end grip member of a dental handpiece, FIG. 1b also showing in election of a neck and head members of the handpiece mounted on the end grip member;

DETAILED DESCRIPTION OF THE INVENTION

Figure 2A:
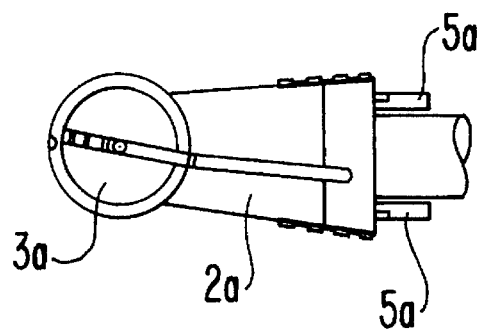
FIGS. 2a–2c are top view of the neck members, each of which are designed as one piece with a respective head member and can be connected selectively, as shown in FIG. 1b, to the end grip member.

An end grip member shown in FIGS. 1a and 1b envelops a drive shaft 11 which drives directly or by way of a gear 12 spur gears 13 and 14, by way of which rotary motion is imparted to a shaft in a tool holder comprising a neck member 2 and head member 3 formed as one piece. A coolant line 4 runs through the end grip member 1 and branches off into two branch lines, of which one branch line 4' terminates in a separating plane between the end grip member 1 and the neck member 2, whereas the other branch line 4" extends as far as the front end of the end grip member 1, wherein a spray is formed from cooling water and also cooling air that is supplied to the end grip member by a supply.

Figure 3A:
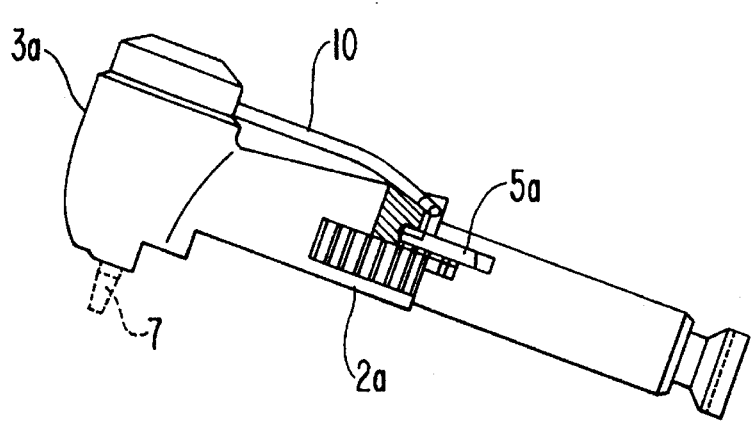
FIGS. 3a–3c are, partially in section, of the members shown in FIGS. 2a–2c, respectively.
Figure 4A:
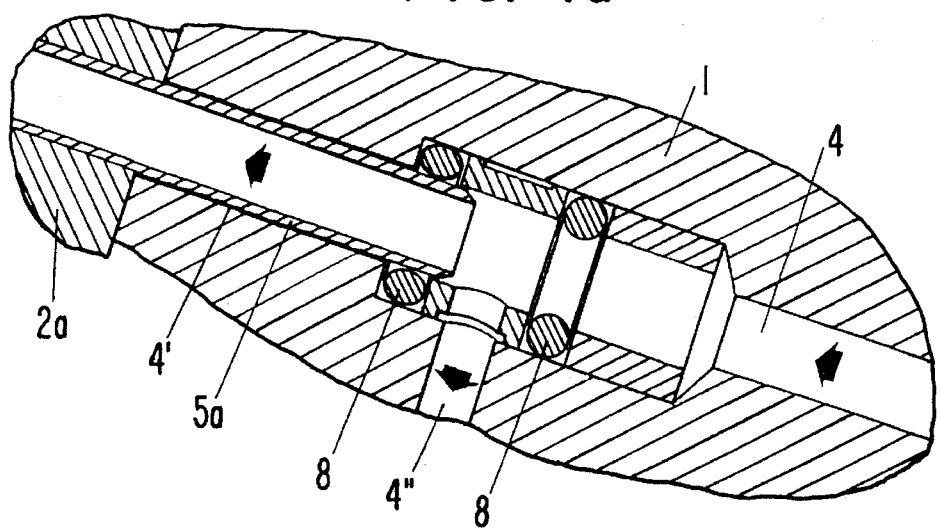
FIGS. 4a–4c are sections depicting points of connection of the end grip member with the members shown in FIGS. 2a–2c, respectively.
Figure 5A:
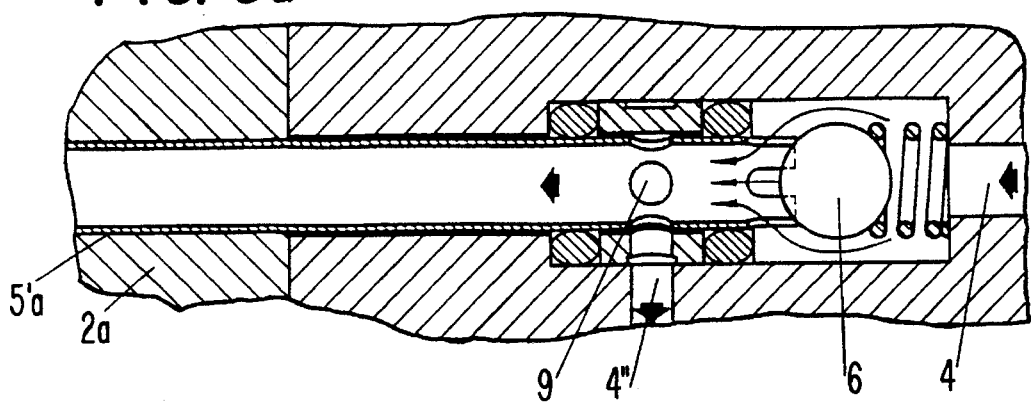
FIGS. 5a–5c are views similar to FIGS. 4a–4c but showing a modification.

Essential for the illustrated end grip member 1 is the possibility of selectively attaching any of a plurality of different tool holders, which are to be supplied in various ways with a cooling medium, in particular cooling water. In the case of the embodiment according to FIGS. 2a and FIG. 3a, the solution is conventional, insofar as the branch line 4' and the branch line 4" of the coolant line contribute to the coolant supply of the instrument. The branch line 4' continues in the hand member 2a in the manner shown in detail in FIGS. 4a and 5a and serves to accomplish an internal cooling of a tool 7 via a line 10. The branch line 4" extends in the manner apparent from FIGS. 1a and 1b to form a cooling spray at the tip of the end grip member 1.

Figure 2B:
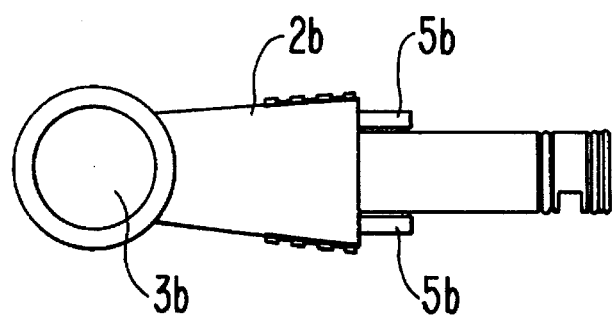
Figure 3B:
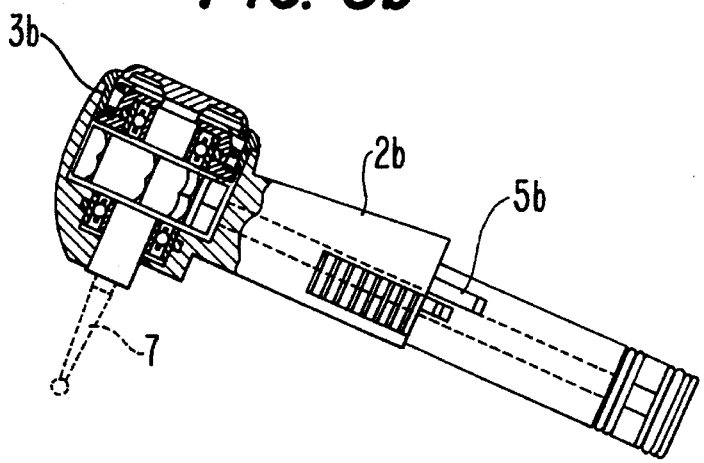

As is evident from FIGS. 2b and 3b, the invention does, however, make is possible to use only a part of the coolant offered by the end grip member 1 by closing the branch line 4' of the coolant line by means of an extension 5b extending into a recess in the end grip member, so that only water for forming a spray is fed only to the top of the grip end 1.

Figure 2C:
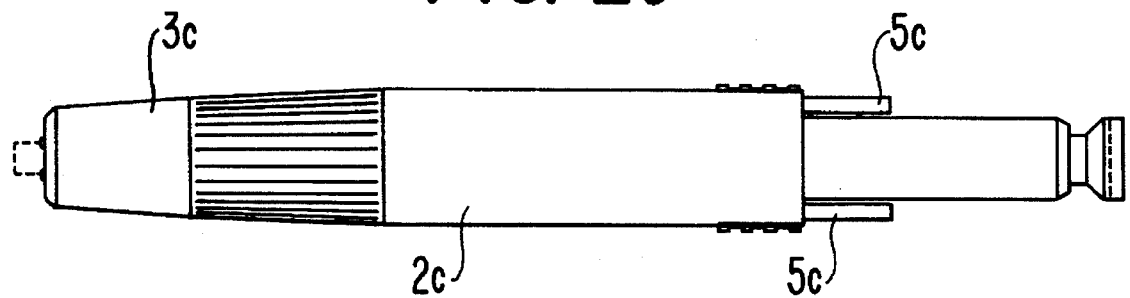
Figure 3C:
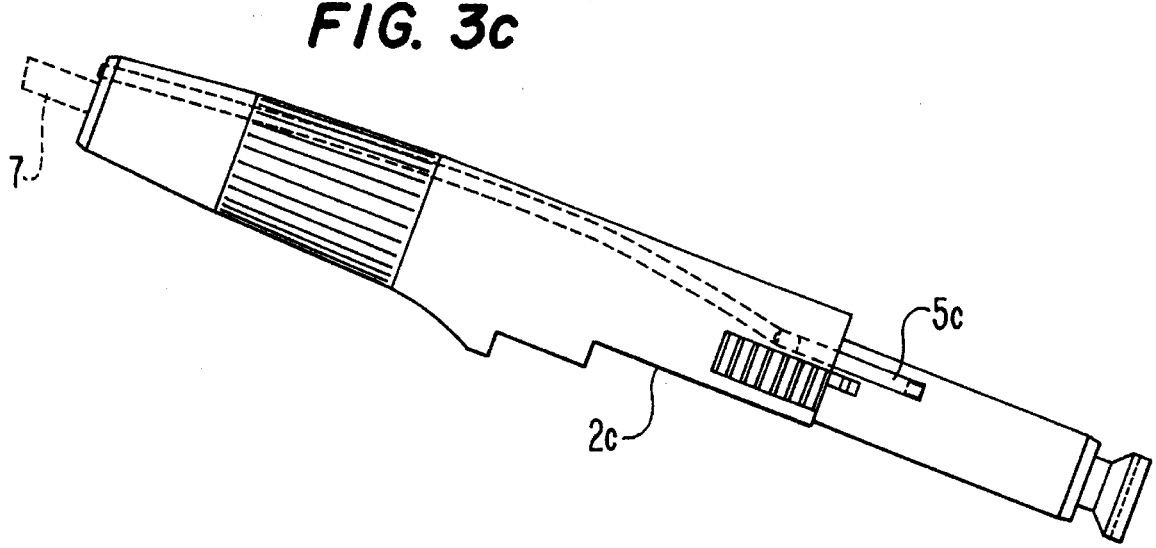
Figure 4B:
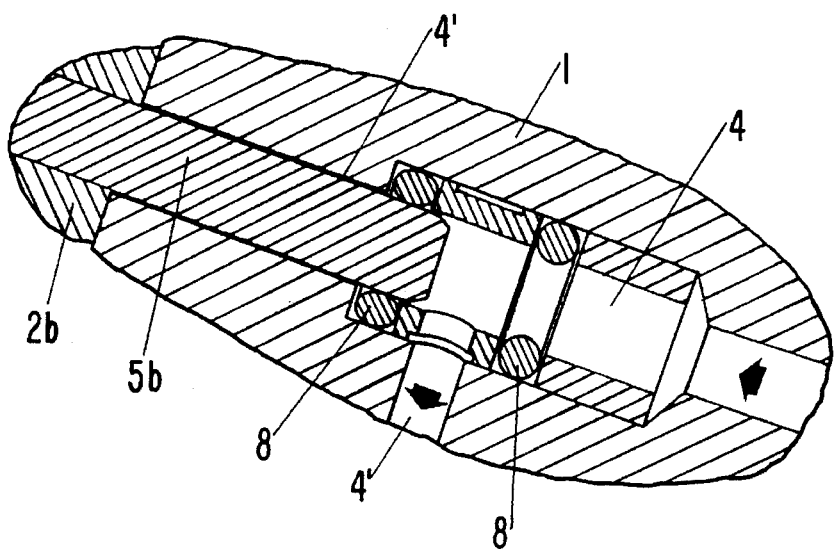
Figure 4C:
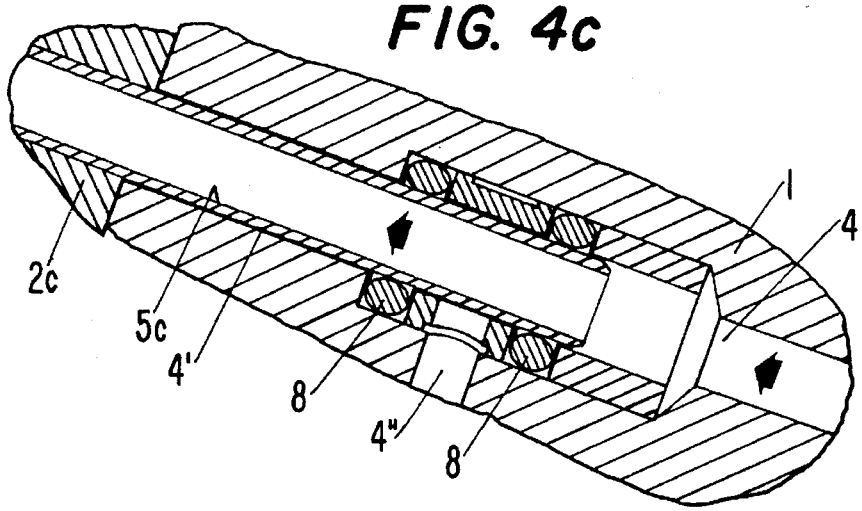

Also, as shown in FIGS. 2c and 3c, it is possible, on the other hand, to continue to run the coolant through an extension 5c, designed according to FIG. 4c, only into the neck member 2c, without providing the possibility of the spray formation at the end of the grip end 1.

Figure 5B:
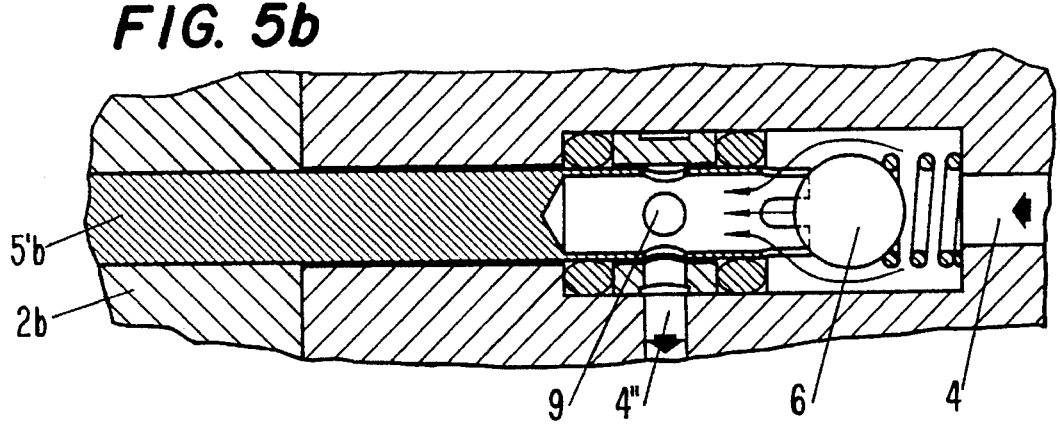
Figure 5C:
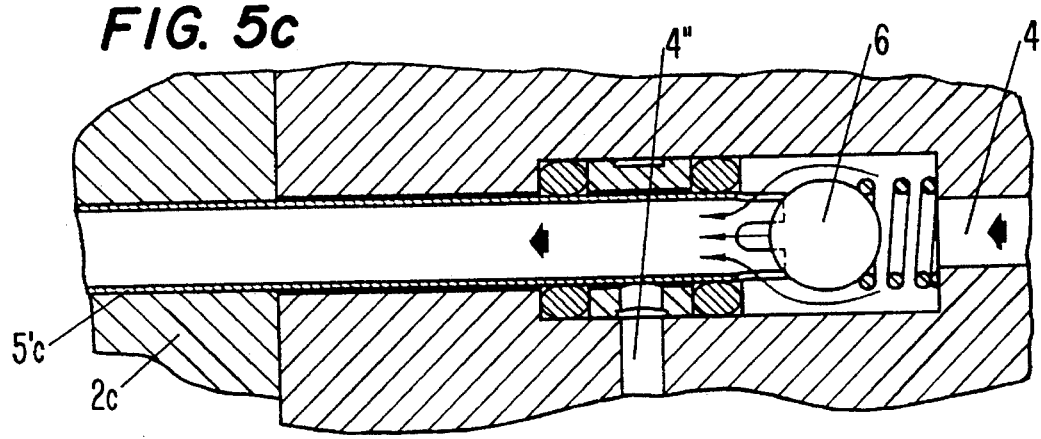
Figure 5D:
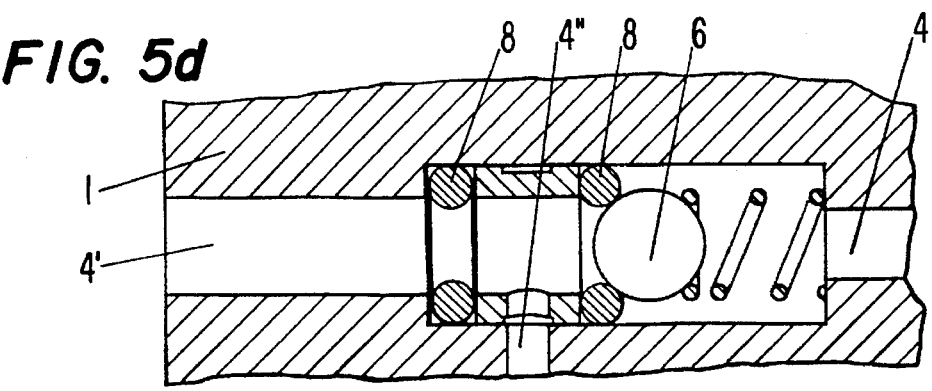
FIG. 5d is a section of the end grip member of the modification without a neck and head member connected thereto.

FIGS. 4a–4c depict the simplest design of the inventive idea. Here, O-rings 8 for sealing are provided at that point where the coolant line divides 4 into two branch lines 4' and 4". The extensions 5a–5c are either designed as bars or tubes. If it is desired that the coolant line 4 be held closed when a tool holder is not attached, such modification can be obtained with the construction shown in FIG. 5d. A valve 6 is provided to maintain the coolant line 4 closed when a tool holder is not attached and that is opened by means of respective extensions 5'a–5'c of the hand members 2a–2c when a tool holder is attached. In so doing, the coolant continues to flow in the case of the embodiment according to FIG. 5a, on the one hand through the extension 5'a, and on the other hand through boreholes 9 in the extension 5' and through branch line 4" of the coolant line. In the case of the embodiment of FIG. 5b, the extension 5'b closes the branch line 4' and opens the inlet to branch line 4". In the embodiment according to FIG. 5c, the branch line 4" is closed and the branch line 4' is supplied with coolant.

I claim:

1. A dental handpiece comprising:

an end grip member having a configuration to be gripped by an operator during use, said end grip member having a first end to be connected to a supply and a second end having therein a recess, and said end grip member having extending therethrough at least one coolant line to receive coolant when said end grip member is connected to the supply; and at least one tool holder selectively connectable to and detachable from said second end of said end grip member, said tool holder having a first end to carry a tool and a second end having an extension which extends into said recess at said second end of said end grip member when said tool holder is connected thereto, said extension having a portion extending into said coolant line and operable to block coolant passage or open coolant passage through a portion of said coolant line.

2. A dental handpiece as claimed in claim 1, comprising a plurality of tool holders each having an extension selectively insertable into said recess.

3. A dental handpiece as claimed in claim 2, wherein each said tool holder comprises a neck member having a respective said extension and a head member to support a respective said tool, said neck member and said head member being formed as an integral one piece structure.

4. A dental handpiece as claimed in claim 1, wherein said end grip member includes internally thereof means for transferring motive power to said tool holder.

5. A dental handpiece as claimed in claim 1, wherein said end grip member has an angled configuration.

6. A dental handpiece as claimed in claim 1, wherein said coolant line has an end at said first end of said end grip member to receive coolant from the supply when said end grip member is connected thereto.

7. A dental handpiece as claimed in claim 6, wherein said coolant line is branched at a position spaced from said end to define first and second branch lines.

8. A dental handpiece as claimed in claim 7, wherein said first branch line forms said recess and said second branch line extends laterally of said first branch line.

9. A dental handpiece as claimed in claim 8, wherein said extension comprises a tube having a length to not block said second branch line when extended into said first branch line, such that coolant is free to flow from said end through both said tube and said second branch line.

10. A dental handpiece as claimed in claim 8, wherein said extension comprises a bar having a length to not block said second branch line when extended into said first branch line, such that coolant is free to flow from said end through said second branch line but is blocked by said bar from flowing through said first branch line.

11. A dental handpiece as claimed in claim 8, wherein said extension comprises a tube having a length to block said second branch line when extended into said first branch line, such that coolant is free to flow from said end through said tube but is blocked by said tube from flowing through said second branch line.

12. A dental handpiece as claimed in claim 8, further comprising a valve closing said coolant line when said extension is not extended into said first branch line.

13. A dental handpiece as claimed in claim 12, wherein said extension has a length, when extended into said first branch line, to extend beyond said second branch line and to open said valve.

14. A dental handpiece as claimed in claim 13, wherein said extension comprises a tube having a lateral opening communicating with said second branch line, such that coolant is free to flow from said end, through said valve and then both through said tube and through said lateral opening and said second branch line.

15. A dental handpiece as claimed in claim 13, wherein said extension comprises a bar blocking said first branch line and having a tubular inner end with a lateral opening communicating with said second branch line, such that coolant is free to flow from said end, through said valve and then through said lateral opening and said second branch line but is blocked by said bar from flowing through said first branch line.

16. A dental handpiece as claimed in claim 13, wherein said extension comprises a tube blocking said second branch line, such that coolant is free to flow from said end, through said valve and then through said tube, but is blocked by said tube from flowing through said second branch line.

* * * * *